US006717000B2

(12) United States Patent
Petersen

(10) Patent No.: US 6,717,000 B2
(45) Date of Patent: Apr. 6, 2004

(54) METHOD FOR THE PREPARATION OF CITALOPRAM

(75) Inventor: Hans Petersen, Vanløse (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/238,843

(22) Filed: Sep. 9, 2002

(65) Prior Publication Data

US 2003/0069304 A1 Apr. 10, 2003

Related U.S. Application Data

(63) Continuation of application No. PCT/DK01/00149, filed on Mar. 7, 2001.

(30) Foreign Application Priority Data

Mar. 13, 2000 (DK) .......................... 2000 00404

(51) Int. Cl.⁷ .......................................... C07D 307/78
(52) U.S. Cl. ............................................... 549/467
(58) Field of Search ........................................ 549/467

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 514/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 6,310,222 B1 | 10/2001 | Ikemoto et al. | 549/467 |
| 6,365,747 B1 | 4/2002 | Dall'Asta et al. | 548/146 |
| 6,392,060 B2 | 5/2002 | Petersen et al. | 549/307 |
| 6,403,813 B1 | 6/2002 | Petersen et al. | 549/305 |
| 6,407,267 B1 | 6/2002 | Rock et al. | 549/467 |
| 6,420,574 B2 | 7/2002 | Petersen et al. | 549/467 |
| 6,426,422 B1 | 7/2002 | Petersen et al. | 549/467 |
| 6,433,196 B1 | 8/2002 | Ikemoto et al. | 549/469 |
| 6,441,201 B1 | 8/2002 | Weber | 549/468 |
| 6,509,483 B2 | 1/2003 | Petersen et al. | |
| 2002/0004604 A1 | 1/2002 | Petersen et al. | 549/462 |
| 2002/0026062 A1 | 2/2002 | Petersen et al. | 549/467 |
| 2002/0035277 A1 | 3/2002 | Rock et al. | 549/467 |
| 2002/0040153 A1 | 4/2002 | Petersen | 549/467 |
| 2002/0061925 A1 | 5/2002 | Petersen et al. | 514/469 |
| 2002/0077353 A1 | 6/2002 | Petersen et al. | 514/469 |
| 2002/0087012 A1 | 7/2002 | Castellin et al. | 549/467 |
| 2002/0120005 A1 | 8/2002 | Villa et al. | 514/466 |
| 2002/0128497 A1 | 9/2002 | Bolzonella et al. | 549/467 |
| 2003/0050484 A1 | 3/2003 | Petersen | |
| 2003/0078442 A1 | 4/2003 | Petersen et al. | |

FOREIGN PATENT DOCUMENTS

| | | | | |
|---|---|---|---|---|
| EP | 1 095 926 | 5/2001 | ........... | C07C/33/46 |
| WO | 98/19511 | 5/1998 | | |
| WO | 98/19512 | 5/1998 | | |
| WO | 98/19513 | 5/1998 | | |
| WO | 99/30548 | 6/1999 | | |
| WO | 00/11926 | 3/2000 | | |
| WO | 00/12044 | 3/2000 | | |
| WO | 00/13648 | 3/2000 | | |
| WO | 00/23431 | 4/2000 | ......... | C07D/307/87 |
| WO | 00/39112 | 7/2000 | ......... | C07D/307/87 |
| WO | 00/44738 | 8/2000 | ......... | C07D/307/88 |
| WO | 01/45483 | 6/2001 | | |
| WO | 01/47877 | 7/2001 | | |
| WO | 01/47909 | 7/2001 | ......... | C07D/307/87 |
| WO | 01/49672 | 7/2001 | ......... | C07D/307/87 |
| WO | 01/51477 | 7/2001 | ......... | C07D/307/87 |
| WO | 01/51478 | 7/2001 | ......... | C07D/307/87 |
| WO | 01/62754 | 8/2001 | ......... | C07D/307/87 |
| WO | 01/66536 | 9/2001 | ......... | C07D/307/87 |
| WO | WO 01/68627 A1 | 9/2001 | | |
| WO | 01/68629 | 9/2001 | ......... | C07D/307/87 |
| WO | WO 01/68630 A1 | 9/2001 | | |
| WO | 01/68631 | 9/2001 | ......... | C07D/307/87 |
| WO | 01/68632 | 9/2001 | ......... | C07D/307/87 |
| WO | WO 01/85712 A1 | 11/2001 | | |
| WO | 02/04435 | 1/2002 | ......... | C07D/307/84 |

OTHER PUBLICATIONS

Bigler, Allan et al., "Quantitative Structure–activity Relationships in a Series of Selective 5–HT uptake inhibitors," *Eur. J. Med. Chem.* 3:289–295 (1997).
Levy, L.F., "4–Aminophthalide and Some Derivatives", *J. Chem. Soc.* pp. 867–870 (1931).
Tirouflet, Jean, "Phtalide Substitués en 5", *Bull. Soc. Sci. de Bretagne* 26:35–43 (1951).
Forney, LeRoy S.., "Reaction of Terephthalic Acid with Formaldehyde in Sulfur Trioxide Media," *J. Org. Chem.* 35:1695–1696 (1970).
Dordor, Isabelle M. et al., "Reaction of Oxazolines with Phosphorus Oxychloride," *Tetrahedron Letters* 24:1437–1440 (1983).
U.S. patent application Ser. No. 10/291,714, Petersen et al., "Method for the Preparation of Citalopram," filed Nov. 8, 2002.
U.S. patent application Ser. No. 09/930,110, Petersen et al., "Method for the Preparation of Citalopram," filed Aug. 14, 2001.

Primary Examiner—Amelia Owens
(74) Attorney, Agent, or Firm—Darby & Darby

(57) ABSTRACT

The present invention relates to a method for the preparation of citalopram comprising reduction of a compound of formula

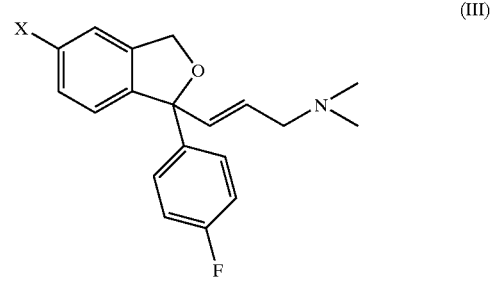

(III)

wherein X is a cyano group or a group which can be converted to a cyano group, and if X is not a cyano group followed by conversion of X to a cyano group.

9 Claims, No Drawings

METHOD FOR THE PREPARATION OF CITALOPRAM

This application is a continuation of International application no. PCT/DK01/00149, filed Mar. 7, 2001. The prior application is hereby incorporated by reference in its entirety.

The present invention relates to a method for the preparation of the well-known antidepressant drug citalopram,1-[3-(dimethylamino)propyl]-1-(4-fluorophenyl)-1,3-dihydro-5-isobenzofurancarbonitrile.

BACKGROUND OF THE INVENTION

Citalopram is a well-known antidepressant drug that has now been on the market for some years and has the following structure:

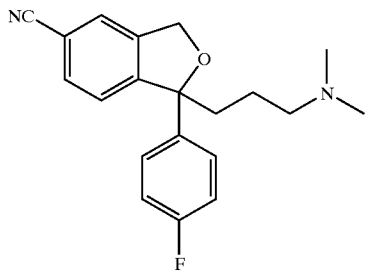

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A-474580.

Citalopram was first disclosed in DE 2,657,013, corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

International patent application No WO 98/019511 discloses a process for the manufacture of citalopram wherein a 4-(cyano, alkyloxycarbonyl or alkylaminocarbonyl)-2-hydroxymethylphenyl-(4-fluorophenyl)methanol compound is subjected to ring closure. The resulting 5-(alkyloxycarbonyl or alkylaminocarbonyl)-1-(4-fluorophenyl)-1,3-dihydroisobenzofuran is converted converted to the corresponding 5-cyano derivative and the 5-cyano derivative is then alkylated with a (3-dimethylamino)propylhalogenide in order to obtain citalopram.

It has now, surprisingly, been found that citalopram may be manufactured by a novel favourable process where 5-cyano-1-(4-fluorophenyl)-1,3-dihydroisobenzofuran is alkylated with a compound which may be converted to a dimethylaminopropyl group.

The alkylation process according to the invention is particularly advantageous because the formation of by-products by polymerisation of the alkylating agent is avoided whereby a reduction in the amount of alkylating reagent to be used is made possible. The process of the invention also provides high yields.

SUMMARY OF THE INVENTION

The present invention relates to a method for the preparation of citalopram, comprising reduction of a compound of formula

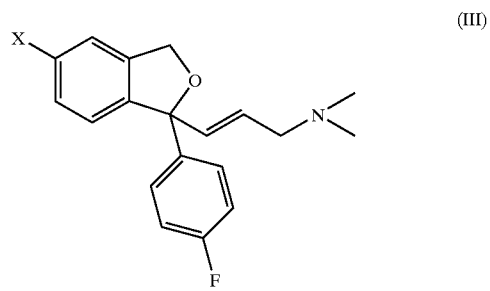

wherein X is a cyano group, or a group which can be converted to a cyano group,
and where X is not a cyano group followed by conversion of X to a cyano group, and isolation of citalopram base or a pharmaceutically acceptable acid addition salt thereof.

In one embodiment of the invention, the compound of formula (III) may be prepared by reaction of a compound of formula

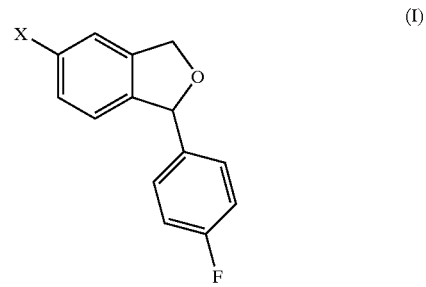

wherein X is as defined above, with a compound of formula

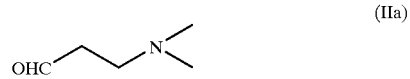

and if X is not cyano, optionally followed by conversion of the group X to a cyano group, thereafter dehydration to form a compound of formula (III) and if X is not cyano, optionally conversion of the group X to a cyano group.

In a second embodiment, the compound of formula (III) may be prepared by reaction of a compound of formula (I) with a compound of formula

and if X is not cyano, optionally followed by conversion of the group X to a cyano group, thereafter dehydration to form a compound of formula (III) and if X is not cyano, optionally followed by conversion of the group X to a cyano group.

In a third embodiment, the compound of formula (III) is prepared by reaction of a compound of formula (I) with a compound of formula

(IIc)

wherein Y is a suitable leaving group, to form a compound of formula

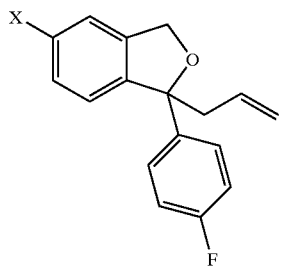
(V)

and if X is not cyano, optionally followed by conversion of the group X to a cyano group, thereafter peroxidation of the double bond to form an epoxide and if X is not cyano, optionally conversion of the group X to a cyano group, thereafter reaction with dimethylamine or a salt thereof followed by dehydration to form a compound of formula (III) and if X is not cyano, optionally followed by conversion of the group X to a cyano group In another aspect, the present invention provides the novel intermediates of the general formula (III) and (V).

In yet another aspect, the present invention relates to an antidepressant pharmaceutical composition comprising citalopram manufactured by the process of the invention.

Suitable leaving groups, Y may be a halogenide or a sulphonate of formula $-O-SO_2-R^0$, wherein $R^0$ is alkyl, alkenyl, alkynyl or optionally alkyl substituted aryl or aralkyl. Conventionally, $R^0$ is methyl or p-methylphenyl.

Groups X, which can be converted to a cyano group may be selected from halogen, $-O-SO_2-(CF)_n-CF_3$, wherein n is 0–8, —CHO, —COOR', —CONR'R", —NHR''' wherein R' and R'' are hydrogen, alkyl, alkenyl or alkynyl, or optionally alkyl substituted aryl or aralkyl and R''' is hydrogen or alkylcarbonyl or X is an oxazoline or thiazoline group of the formula

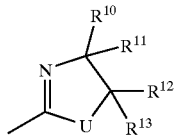
(VI)

wherein U is O or S;
$R^{12}-R^{13}$ are each independently selected from hydrogen and alkyl, or $R^{12}$ and $R^{13}$ together form a $C_{2-5}$ alkylene chain thereby forming a spiro-ring; $R^{10}$ is selected from hydrogen and alkyl, $R^{11}$ is selected from hydrogen, alkyl, a carboxy group or a precursor group therefore, or $R^{10}$ and $R^{11}$ together form a $C_{2-5}$ alkylene chain thereby forming a spiro-ring.

X may be any other group which can be converted to a cyano group.

The alkylation step where the compound of formula I is reacted with a compound of formula (IIa), (IIb) or (IIc) is suitably carried out by treatment of the compound of formula (I) with a base such as for example LDA (lithiumdiisopropylamine), LiHMDS (hexamethyldisilasan lithium), NaH, NaHMDS (hexamethyldisilasan sodium) and metalalkoxides such as NaOMe, KOMe, LiOMe, NaOtertBu, KOtertBu and LiOtertBu in an aprotic organic solvent such as THF (tetrahydrofuran), DMF (dimethylformamide), NMP (N-methylpyrrolidon), ethers such as diethylether or dioxalane, toluene, benzene, or alkanes and mixtures thereof. The anion formed is then reacted with a compound of formula (IIa), (IIb) or (IIc).

The reaction of the compound of formula (I) with a compound of formula (IIa), (IIb) or (IIc) is suitably carried out under non-aqueous conditions.

The dehydration of the intermediate alcohol, formed by reaction of the compound of formula (I) with a compound of formula (IIa) or (IIb), to form a compound of formula (III) may be carried out with any suitable dehydrating agent, e.g. with p-toluenesulfonic acid in toluene or with $SOCl_2$, $POCl_3$, $PCl_5$, mineral acids etc.

The peroxidation of the alkene double bond in a compound of formula (V) to form an epoxide may be carried out using tertBuOOH, organic peracids, dimethyldioxirane, NaOCl, $I_2$/Ago, microorganisms etc. After reaction with dimethylamine or a salt thereof, the resulting compound is subjected to dehydration using any suitable dehydrating agent, e.g. with p-toluenesulfonic acid in toluene or with $SOCl_2$, $POCl_3$, $PCl_5$, mineral acids etc.

The reduction of the compound of formula (III) is suitably carried out in presence of Pd/C, Pt/C or Rh/C as catalyst.

When X is halogen or $CF_3-(CF_2)_n-SO_2-O-$, wherein n is 0–8, the conversion to a cyano group may be carried out by reaction with a cyanide source, for example KCN, NaCN, CuCN, $Zn(CN)_2$ or $(R^{15})_4NCN$, where $(R^{15})_4$ indicates four groups, which may be the same or different, and are selected from hydrogen and straight chain or branched alkyl, in the presence of a palladium catalyst and a catalytic amount of $Cu^{+ \, or \, Zn^{2+}}$, or with $Zn(CN)_2$ in the presence a palladium catalyst. The conversion of a compound wherein X is halogen or $CF_3-(CF_2)_n-SO_2-O-$, wherein n is 0–8, by reaction with a cyanide source in presence of a palladium catalyst, may be carried out as described in WO 0013648.

When X is Cl or Br the conversion to a cyano group may also be carried out by reaction with a cyanide source, for example KCN, NaCN, CuCN, $Zn(CN)_2$ or $(R^{15})_4NCN$, where $(R^{15})_4$ indicates four groups, which may be the same or different, and are selected from hydrogen and straight chain or branched alkyl, in the presence of a nickel catalyst. The conversion of a compound wherein X is halogen or $CF_3-(CF_2)_n-SO_2-O-$, wherein n is 0–8, by reaction with a cyanide source in presence of a nickel catalyst may be carried out as described in WO 001192.

The reactions may be performed in any convenient solvent as described in Sakakibara et. al. *Bull. Chem. Soc. Jpn.*, 61, 1985–1990, (1988). Preferred solvents are acetonitrile, ethylacetate, THF, DMF or NMP.

When X is an oxazoline or a thiazoline of the formula (VI), the conversion to a cyano may be carried out as described in WO 0023431.

When X is CHO, the conversion to a cyano group may be carried out by conversion of the formyl group to an oxime or similar group by reaction with a reagent $R^{16}-V-NH_2$, wherein $R^{16}$ is hydrogen, alkyl, aryl or heteroaryl and V is O, N or S, followed by dehydration with a common dehydrating agent, for example thionylchloride, acetic anhydride/pyridine, pyridine/HCl or phosphor pentachloride. Preferred reagents $R^{16}$—V—$NH_2$, are hydroxylamine and compounds wherein $R^{16}$ is alkyl or aryl and V is N or O.

When X is —COOH, the conversion to a cyano group may be carried out via the corresponding acid chloride or ester and amide.

The acid chloride is conveniently obtained by treatment of the acid with $POCl_3$, $PCl_5$ or $SOCl_2$ neat or in a suitable solvent, such as toluene or toluene comprising a catalytic amount of N,N-dimethylformamide. The ester is obtained by treatment of the acid with an alcohol, in the presence of an acid, preferably a mineral acid or a Lewis acid, such as HCl, $H_2SO_4$, $POCl_3$, $PCl_5$ or $SOCl_2$. Alternatively, the ester may be obtained from the acid chloride by reaction with an alcohol. The ester or the acid chloride is then converted to an amide by amidation with ammonia or an alkylamine, preferably t-butyl amine.

The conversion to amide may also be obtained by reaction of the ester with ammonia or an alkylamine under pressure and heating.

The amide group is then converted to a cyano group by dehydration. The dehydrating agent may be any suitable dehydrating agent, and the optimal agent may easily be determined by a person skilled in the art. Examples of suitable dehydrating agents are $SOCl_2$, $POCl_3$ and $PCl_5$, preferably $SOCl_2$.

In a particularly preferred embodiment, the carboxylic acid is reacted with an alcohol, preferably ethanol, in the presence of $POCl_3$, in order to obtain the corresponding ester, which is then reacted with ammonia thereby giving the corresponding amide, which in turn is reacted with $SOCl_2$ in toluene comprising a catalytic amount of N,N-dimethylformamide.

Alternatively, a compound where X is —COOH may be reacted with chlorosulfonyl isocyanate in order to form the nitrile, or treated with a dehydrating agent and a sulfonamide as described in WO 0044738.

When X is —NHR''', where R''' is hydrogen, the conversion to cyano is preferably performed by diazotation and followed by reaction with $CN^-$. Most preferably $NaNO_2$ and CuCN and/or NaCN is used. When R''' is alkylcarbonyl, the compound is initially subjected to hydrolysis thereby obtaining the corresponding compound wherein R''' is H, which is then converted as described above. The hydrolysis may be performed either in acidic or basic environment.

Starting materials of formula (I) wherein X is halogen may be prepared as described in GB 1526331, compounds of formula (I) wherein X is —O—$SO_2$—$(CF_2)_n$—$CF_3$ may be prepared analogously to the compounds described in WO 99/00640, compounds of formula (I) wherein X is an oxazoline or a thiazoline group may be prepared analogous to the compounds described in WO 0023431, compounds wherein X is formaldehyde may be prepared analogously to the compounds described in as WO 99/30548, compounds wherein X is —COOH, and esters and amides thereof may be prepared analogously to the compounds described in WO 98/19511 and compounds of formula I wherein X is —NIR''' may be prepared analogously to the compounds described in WO 98/19512.

The reaction conditions, solvents, etc. used for the reactions described above are conventional conditions for such reactions and may easily be determined by a person skilled in the art.

The starting material of formula (I) wherein X is cyano may be prepared as described in U.S. Pat. No. 4,136,193 or as described in WO 98/019511.

The compounds of formula (IIa), (IIb) and (IIc) are commercially available or may be prepared from commercially available starting materials using conventional techniques.

Citalopram is on the market as an antidepressant drug in the form of the racemate. However, in the near future the active S-enantiomer of citalopram is also going to be introduced to the market.

S-citalopram may be prepared by separation of the optically active isomers by chromatography.

Throughout the specification and claims, the term alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Similarly, alkenyl and alkynyl, respectively, designate such groups having from two to six carbon atoms, including one double bond or triple bond respectively, such as ethenyl, propenyl, butenyl, ethynyl, propynyl and butynyl.

The term aryl refers to a mono- or bicyclic carbocyclic aromatic group, such as phenyl and naphthyl, in particular phenyl.

The term aralkyl refers to aryl-alkyl, wherein aryl and alkyl are as defined above.

Optionally alkyl substituted aryl and aralkyl refer to aryl and aralkyl groups which may optionally be substituted with one or more alkyl groups.

Halogen means chloro, bromo or iodo.

Citalopram may be used as the free base, preferably in crystalline form, or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of citalopram may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive, colourings, aroma, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling in suitable ampoules or vials. Any suitable additive conventionally used in the art may be added, such as tonicity agents, preservatives, antioxidants, etc.

The invention is further illustrated by the following examples.

EXAMPLE 1

A solution of 1-(4-fluorophenyl)-1,3-dihydroisobenzofuran-5-carbonitrile (4.8 g, 0.02 mol) in THF (50 mL) was added dropwise to a solution of LDA (Butyl lithium 1.6 M (15 mL), disopropylamine 2.6 g) at −30° C. under an atmosphere of nitrogen. After stirring at −30° C. for 10 minutes, a solution of a compound of formula (IIa), (IIb) or (IIc) (0.02 mol) in THF (25 mL) was added dropwise and allowed to warm to room temperature and stirred for a further 60 minutes. The reaction was then quenched with ice, extracted with toluene (3×50 mL), washed with water (50 mL) and concentrated under reduced pressure. The residue was purified by chromatography on silica gel using mixtures of n-heptane/EtOAc as the eluent.

What is claimed is:

1. A method for the preparation of citalopram comprising reducing a compound of formula

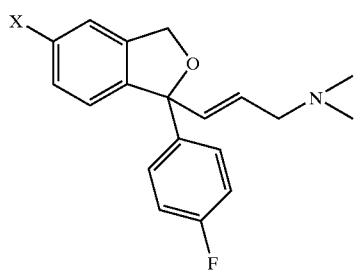

(III)

wherein X is a cyano group, or a group which can be converted to a cyano group, and where X is not a cyano group followed by converting X to a cyano group; and isolating citalopram in the form of the base or a pharmaceutically acceptable acid addition salt thereof.

2. The method according to claim 1 wherein the compound of formula (III) is prepared by reacting a compound of formula

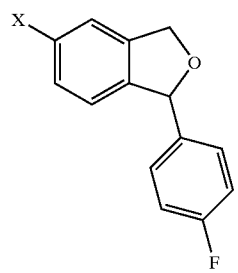

(I)

wherein X is as defined above, with a compound of formula

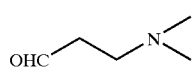

(IIa)

and if X is not cyano, optionally followed by converting X to a cyano group, thereafter dehydrating to form a compound of formula (III) and if X is not cyano, optionally followed by converting X to a cyano group.

3. The method according to claim 1 wherein the compound of formula (III) is prepared by reacting a compound of formula

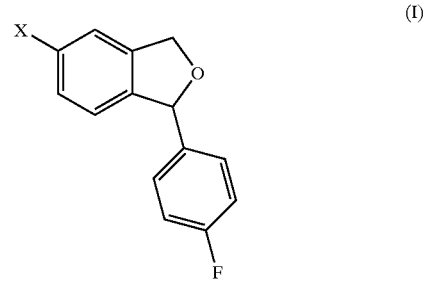

(I)

wherein X is as defined above, with a compound of formula

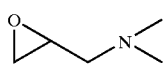

(IIb)

and if X is not cyano, optionally followed by converting X to a cyano group, thereafter dehydrating to form a compound of formula (III) and if X is not cyano, optionally followed by converting X to a cyano group.

4. The method according to claim 1 wherein the compound of formula (III) is prepared by reacting a compound of formula

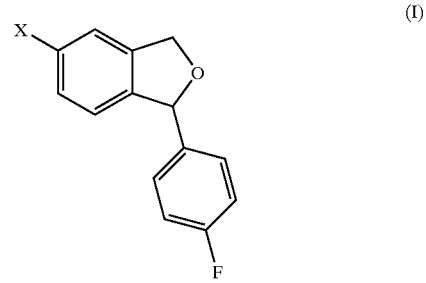

(I)

wherein X is as defined above, with a compound of formula

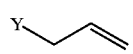

(IIc)

to form a compound of formula

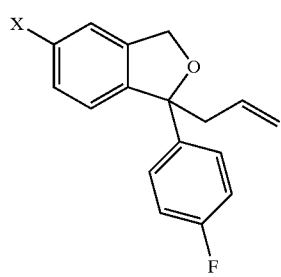

(V)

and if X is not cyano, optionally followed by converting X to a cyano group, thereafter performing peroxidation of the double bond to form an epoxide, and if X is not cyano, optionally converting X to a cyano group, and reacting with dimethyl amine or a salt thereof, followed by dehydration to form a compound of formula (III), and if X is not cyano optionally followed by converting X to a cyano group.

5. A compound having the formula

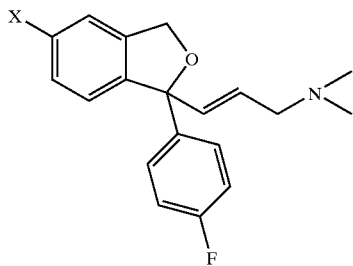

(III)

wherein X is a cyano group, or a group which can be converted to a cyano group, or an acid addition salt thereof.

6. A compound having the formula

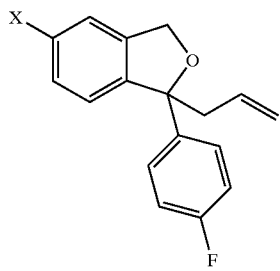

(V)

wherein X is a cyano group, or a group which can be converted to a cyano group, or an acid addition salt thereof.

7. The method of claim 1, wherein X is a cyano group or a group which may be converted to a cyano group which is selected from the group consisting of a halogen, $-O-SO_2-(CF_2)_n-CF_3$, where n is 0–8, -CHO; -COOR', -CONR'R" or NHR'" where R' and R" are selected from hydrogen, alkyl, alkenyl, alkynyl or optionally alkyl substituted aryl or aralkyl and R'" is hydrogen or alkylcarbonyl, or X is a group of formula

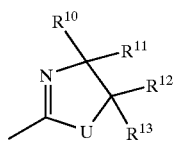

(VI)

wherein U is O or S;
R$^{12}$ and R$^{13}$ are each independently selected from hydrogen and alkyl, or R$^{12}$ and R$^{13}$ together from a C$_{2-5}$ alkylene chain thereby forming a spiro ring; R$^{10}$ is selected from hydrogen and alkyl, R$^{11}$ is selected from hydrogen, alkyl, a carboxy group or a precursor group therefore, or R$^{10}$ and R$^{11}$ together form a C$_{2-5}$ alkylene chain thereby forming a spiro ring.

8. The compound of claim 5, wherein X is a cyano group or a group which may be converted to a cyano group which is selected from the group consisting of halogen, $-O-SO_2-(CF_2)_n-CF_3$, wherein n is 0–8, -CHO, -COOR', -CONR'R" or NHR'" wherein R' and R" are selected from hydrogen, alkyl, alkenyl, alkynyl or optionally alkyl substituted aryl or aralkyl and R'" is hydrogen or alkylcarbonyl, or X is a group of formula

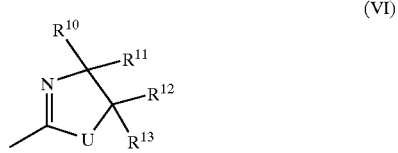

(VI)

wherein U is O or S;
R$^{12}$ and R$^{13}$ are each independently selected from hydrogen and alkyl, or R$^{12}$ and R$^{13}$ together form a C$_{2-5}$ alkylene chain thereby forming a spiro ring; R$^{10}$ is selected from hydrogen and alkyl, R$^{11}$ is selected from hydrogen, alkyl, a carboxy group or a precursor group therefore, or R$^{10}$ and R$^{11}$ together form a C$_{2-5}$ alkylene chain thereby forming a spiro ring.

9. The compound of claim 6, wherein X is a cyano group or a group which may be converted to a cyano group which is selected from the group consisting of halogen, $-O-SO_2-(CF_2)_n-CF_3$, wherein n is 0–8, -CHO, -COOR', -CONR'R" or NHR'" wherein R' and R" are selected from hydrogen, alkyl, alkenyl, alkynyl or optionally alkyl substituted aryl or aralkyl or R'" is hydrogen or alkylcarbonyl, or X is a group of formula

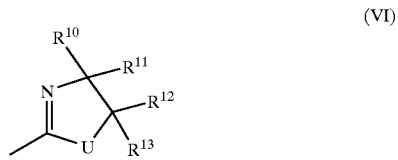

(VI)

wherein U is O or S;
R$^{12}$ and R$^{13}$ are each independently selected from hydrogen and alkyl, or R$^{12}$ and R$^{13}$ together form a C$_{2-5}$ alkylene chain thereby forming a spiro ring; R$^{10}$ is selected from hydrogen and alkyl, R$^{11}$ is selected from hydrogen, alkyl, a carboxy group or a precursor group therefore, or R$^{10}$ and R$^{11}$ together form a C$_{2-5}$ alkylene chain thereby forming a spiro ring.

* * * * *